United States Patent [19]

Fung

[11] Patent Number: 4,567,273

[45] Date of Patent: Jan. 28, 1986

[54] LIQUID PHASE HALOGEN EXCHANGE OF (TRICHLOROMETHYL) PYRIDINES TO (TRIFLUOROMETHYL)PYRIDINES

[75] Inventor: Alexander P. Fung, Pleasant Hill, Calif.

[73] Assignee: The Dow Chemical Company, Midland, Mich.

[21] Appl. No.: 589,433

[22] Filed: Mar. 14, 1984

Related U.S. Application Data

[63] Continuation of Ser. No. 369,051, Apr. 16, 1982, abandoned.

[51] Int. Cl.$^4$ ............................................ C07D 213/26
[52] U.S. Cl. ..................................... 546/345; 546/346
[58] Field of Search ................ 546/345, 346; 570/161, 570/166, 168, 170

[56] References Cited

U.S. PATENT DOCUMENTS 2,442,290  5/1948  Halbedel et al. ................. 260/465.7
4,288,290  9/1981  Nishiyama et al. ................. 546/345

OTHER PUBLICATIONS

Henne, Journal of the American Chemical Society, vol. 60, pp. 1569–1571, 1938.
Fieser & Fieser, Reagents for Organic Synthesis, vol. 6, pp. 514–515, 1977.

Primary Examiner—Alan L. Rotman

[57] ABSTRACT

(Trifluoromethyl)pyridine compounds are prepared in high yields and with a high selectivity by using a mercury or silver fluorinating agent, i.e., $HgF_2$, $AgF$, $AgF_2$, in a liquid phase halogen exchange process.

19 Claims, No Drawings

LIQUID PHASE HALOGEN EXCHANGE OF (TRICHLOROMETHYL) PYRIDINES TO (TRIFLUOROMETHYL)PYRIDINES

CROSS-REFERENCE TO RELATED APPLICATION

This is a continuation of application Ser. No. 369,051, filed Apr. 16, 1982, now abandoned.

BACKGROUND OF THE INVENTION

The present invention relates to a method of preparing (trifluoromethyl)pyridine compounds in a highly selective manner by reacting (trichloromethyl)pyridine compounds with mercury or silver fluorinating agents in a liquid phase halogen exchange reaction.

Fluorination of (trichloromethyl)pyridine compounds has been carried out by vapor phase fluorination which requires the use of high temperatures. Such vapor phase reactions suffer from disadvantages including, for example, energy costs associated with elevating the temperature of the reactants. Additionally, at the temperature necessary for the fluorination reaction, both the starting materials and the end products can be decomposed or converted into undesirable by-products which lead to low conversions and low selectivities to the desired (trifluoromethyl)pyridine products. See, for example, U.S. Pat. Nos. 4,266,064 and 4,288,599.

Another method of preparing (trifluoromethyl)pyridine compounds has been to contact a (trichloromethyl)pyridine compound with antimony trifluorodichloride ($SbF_3Cl_2$). See, for example, U.S. Pat. Nos. 3,136,822; 3,787,420; and 3,818,019. The disadvantages associated with this reaction are, for example, the difficulty in controlling an extremely exothermic reaction, the high cost of antimony trifluoride and the difficulty in recycling the antimony by-product. Thus, it is evident that a more efficient method of preparing (trifluoromethyl)pyridine compounds is desirable.

It has been unexpectedly found that mercury and silver fluorinating agents convert (trichloromethyl)pyridine compounds into (trifluoromethyl)pyridine compounds in high yields with a high selectivity to the desired (trifluoromethyl)pyridine compounds in liquid phase halogen exchange reactions conducted at low temperatures.

SUMMARY OF THE INVENTION

Briefly, in accordance with the present invention, a (trifluoromethyl)pyridine compound can be prepared in high yield and in a highly selective manner by the halogen (fluorine-chlorine) exchange of an appropriate (trichloromethyl)pyridine compound. The (trichloromethyl)pyridine compound containing one or two trichloromethyl groups may optionally have substituents in other pyridine ring positions in addition to the trichloromethyl substituents.

The present method comprises contacting a (trichloromethyl)pyridine compound with a mercury or silver fluorinating agent under conditions sufficient to form the desired (trifluoromethyl)pyridine compound in a high yield and in a highly selective manner. This highly selective halogen exchange reaction is surprising in that it occurs only when mercury and silver fluorinating agents, described herein, are employed. Other fluorinating agents have not been found to selectively fluorinate (trichloromethyl)pyridine compounds to the degree found with the mercury or silver fluorinating agents.

Of particular interest in the practice of the present invention is a method of preparing a β-(trifluoromethyl)pyridine compound, such as, for example, preparing 2,3-dichloro-5-(trifluoromethyl)pyridine from 2,3-dichloro-5-(trichloromethyl)pyridine. 2,3-Dichloro-5-(trifluoromethyl)pyridine is useful as an intermediate in the manufacture of herbicides. Also of interest is a method of preparing 2-chloro-5-(trifluoromethyl)pyridine from 2-chloro-5-(trichloromethyl)pyridine which is useful as an intermediate in the manufacture of herbicides.

DETAILED DESCRIPTION OF THE EMBODIMENTS

In the practice of the present invention it is essential to employ: a (trichloromethyl)pyridine compound and a mercury or silver fluorinating agent.

(Trichloromethyl)pyridine compounds employed as the starting material are unsubstituted or substituted-(trichloromethyl)pyridine compounds containing one or two trichloromethyl groups. The pyridine ring optionally contains other substituents, besides the $CCl_3$ groups, which do not affect the halogen exchange reaction of this invention. Such substituents include, for example, Cl, Br, I, or F. A preferred (trichloromethyl)pyridine compound is a β-(trifluoromethyl)pyridine, such as, 2,3-dichloro-5-(trichloromethyl)pyridine.

The (trichloromethyl)pyridine compounds, described herein are known compounds and are prepared in any of a number of well known procedures. U.S. Pat. Nos. 3,787,420; 3,743,648; 4,184,041 and 3,818,019, all of which are incorporated herein by reference, disclose methods of preparing (trichloromethyl)pyridines and halo(trichloromethyl)pyridines.

The second essential component for the practice of the present invention is a mercury or silver fluorinating agent. Suitable fluorinating agents include mercuric fluoride ($HgF_2$), mercurous fluoride ($Hg_2F_2$), silver fluoride (AgF) and silver difluoride ($AgF_2$). These fluorinating agents are contacted with the (trichloromethyl)pyridine compound to form the desired product. While the present halogen exchange reaction can be carried out neat, it is preferred to employ a solvent which acts as a reaction medium. Common organic solvents, such as, for example, benzene and xylene, are acceptable, while the preferred solvent is liquid hydrogen fluoride.

In a preferred operation the fluorinating agents are formed in situ by the addition of a mercury or silver precursor compound that will react with the hydrogen fluoride solvent in the reaction mixture to form the hereinbefore described fluorinating agents. Such mercury and silver precursor compounds include red mercuric oxide, yellow mercuric oxide, mercuric chloride, mercuric carbonate, silver chloride, silver oxide and silver carbonate. The fluorinating agents are advantageously supplied in the present reaction in stoichiometric amounts.

The mercury and silver fluorinating agents and precursor compounds described above are all known compounds and are commercially available.

Hydrogen fluoride, the preferred solvent employed in the practice of the present invention, is introduced into the present method as hydrogen fluoride (anhydrous) or as hydrofluoric acid. Hydrogen fluoride (anhydrous) has a boiling point of 19.5° C. and the liquid and gas consist of associated molecules. Hydrogen fluoride (anhydrous) is a well-known compound and commercially available, generally in cyclinders and tank cars. The hydrogen fluoride is introduced into the present reaction either as a liquid or as a gas.

When introducing hydrogen fluoride into the present reaction as a gas, it is advantageous to liquify the hydrogen fluoride so that it can form a reaction mixture with the (trichloromethyl)pyridine starting material. In order to liquify gaseous hydrogen fluoride the temperature is regulated to be compatible with liquid hydrogen fluoride, i.e., below 19.5° C. A preferred means of liquifying hydrogen fluoride (anhydrous) is to condense the hydrogen fluoride at temperatures below about 0° C. and even more preferably at a temperature of about −20° C. Liquid hydrogen fluoride is also supplied as hydrofluoric acid which is hydrogen fluoride in aqueous solution. Hydrofluoric acid, when in a gaseous state, is condensed into a liquid employing procedure described above for condensing hydrogen fluoride (anhydrous). In the practice of the present invention, it is preferred to employ hydrogen fluoride (anhydrous) as the source of liquid hydrogen fluoride.

In conducting the present halogen exchange reaction the aforementioned essential components are admixed, resulting in the formation of the desired (trifluoromethyl)pyridine product. When a solvent is employed, the order of admixing the reactants is not essential but it is preferred to first admix the (trichloromethyl)pyridine compound with the solvent and thereafter add the mercury or silver fluorinating agent or the precursor compound thereto. To ensure thorough contacting of the (trichloromethyl)pyridine with the fluorinating agent, the reaction mixture is advantageously kept in an agitated state by conventional means, such as by shaking or stirring.

In a preferred manner of conducting the present halogen exchange reaction, a (trichloromethyl)pyridine compound is mixed with liquid hydrogen fluoride (anhydrous). Advantageously, the hydrogen fluoride is condensed at a temperature below its boiling point of 19.5° C. and preferably at a temperature between about 0° C. and about −20° C. The condensed liquid hydrogen fluoride and the (trichloromethyl)pyridine compound form remarkably stable solutions when mixed in molar ratios advantageously in the range of from about 4 to about 18 molar equivalents of hydrogen fluoride per molar equivalent of (trichloromethyl)pyridine compound and preferably in the range of from about 8 to about 12. An especially preferred molar ratio is about 9 molar equivalents of hydrogen fluoride per molar equivalent of (trichloromethyl)pyridine compound. The hydrogen fluoride/(trichloromethyl)pyridine mixtures thus produced are generally stable solutions at temperatures up to about 50° C.

Once the hydrogen fluoride/(trichloromethyl)pyridine solution is prepared, the mercury or silver fluorinating agent, described herein, is added thereto, with agitation. The mercury or silver fluorinating agent is added in at least stoichiometric quantities to ensure complete conversion of the (trichloromethyl)pyridine compound. For example, when $HgF_2$ is employed as the fluorinating agent about 1.5 molar equivalents of $HgF_2$ are added per molar equivalent of mono-(trichloromethyl)pyridine compound present in the reaction mixture and when AgF is employed as the fluorinating agent about 3 molar equivalents of AgF are added per molar equivalent of mono-(trichloromethyl)pyridine compound present in the reaction mixture. When bis-(trichloromethyl)pyridine compounds are employed as starting materials, twice the molar amount of fluorinating agents are required to fluorinate both trichloromethyl groups as compared to the amount required to fluorinate a single trichloromethyl group, i.e. about 3 molar equivalents of $HgF_2$ and about 6 molar equivalents of HgF are needed to fluorinate bis-(trichloromethyl)pyridine compounds. The fluorinating agents are added to the reaction mixture slowly so that the exotherm of the reaction mixture does not exceed about 50° C. and preferably does not exceed about 35° C.

Preferably, the mercury and silver fluorinating agents are formed in situ by the addition of a mercury or silver precursor compound, described hereinbefore, to the hydrogen fluoride/(trichloromethyl)pyridine reaction mixture. The addition of such precursor compound is advantageously accompanied with continuous agitation of the reaction mixture. The precursor compound thus added to the reaction mixture reacts with the hydrogen fluoride to form the fluorinating agent which in turn reacts with the (trichloromethyl)pyridine compound to form the desired (trifluoromethyl)pyridine product. The mercury or silver precursor compounds are advantageously added in amounts sufficient to form at least a stoichiometric quantity of mercury or silver fluorinating agent so that substantially all of the (trichloromethyl)pyridine starting material is consumed in the reaction.

The precursor compound is added at a rate so that the temperature of the reaction mixture does not exceed about 50° C. and preferably at a rate so that the temperature of the reaction mixture does not exceed about 35° C.

While the exact pressure at which the present halogen exchange reaction is carried out is not critical, it is conveniently conducted at ambient atmospheric pressure.

Generally, the halogen exchange reactions described herein are complete in from about 2 to about 36 hours. Upon completion, the desired (trifluoromethyl)pyridine product is isolated using conventional separatory techniques such as solvent extraction with an organic solvent, such as, for example, methylene chloride.

After separation of the desired (trifluoromethyl)pyridine product, the mercury or silver by-products formed are treated for recycling back into the reaction process employing known procedures. For example, when $HgCl_2$ is a by-product of the present halogen exchange process, it is collected and treated with aqueous NaOH to form HgO which is then re-introduced into the halogen exchange process as a precursor compound.

The present halogen exchange reaction is characterized by the following chemical equation:

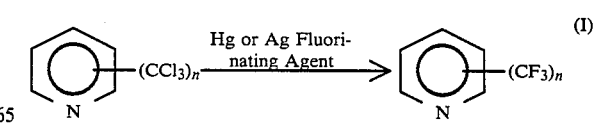

(I)

wherein n represents the integers 1 or 2. Some preferred reactions are characterized as follows:

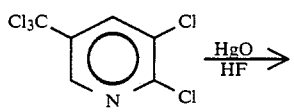
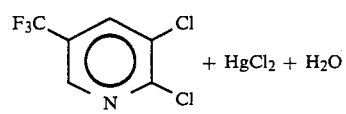

(II)

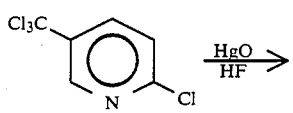
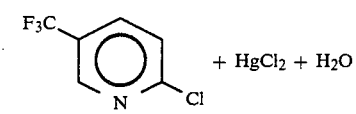

(III)

No attempt has been made to balance the above equations. In Equation (I) above, the (trichloromethyl)pyridine compound may be further substituted as hereinbefore described and in Equations (II) and (III) the HgO is added as a mercury precursor compound which reacts with the HF to form enough HgF₂ in situ to react with substantially all of the starting material.

The following examples illustrate the practice of the present invention but, as such, should not be construed as limitations upon the overall scope of the same.

EXAMPLE 1

Into a 500 milliliter (ml) polyethylene bottle, equipped with a condenser and a stirring means, was placed 106.16 grams (g) (0.4 mole) of 2,3-dichloro-5-(trichloromethyl)pyridine and 180 g (9 moles) of anhydrous hydrogen fluoride which was condensed at −20° C. This mixture was initially kept at −20° C. in order to keep the hydrogen fluoride in a liquid phase. To this reaction mixture 130 g (0.6 mole) of red, mercuric oxide was slowly added over a three hour period, with stirring, so that the temperature of the reaction mixture did not exceed 35° C. The reaction mixture at first appeared red in color but progressively faded to pink, yellow, grayish white and then finally to gleaming white. The gleaming white appearance of the reaction mixture indicated the reaction was complete and occurred in about 22 hours. Upon completion, the reaction mixture was filtered and the filtrate was neutralized with NaHCO₃ and the desired product extracted with methylene chloride and then dried over anhydrous MgSO₄. The methylene chloride was then removed under reduced pressure leaving the desired product 2,3-dichloro-5-(trifluoromethyl)pyridine as a colorless liquid having a boiling point of 171°–173° C. Analysis, via standard gas-liquid chromatography procedures, indicated approximately 100% conversion of the starting material with 98% selectivity to the desired 2,3-dichloro-5-(trifluoromethyl)pyridine.

EXAMPLE 2

Substantially the same procedure employed in Example 1 was followed except that the reagents listed in Table 1 were added in stoichiometric amounts to the reaction mixture (2,3-dichloro-5-(trichloromethyl)pyridine and liquid hydrogen fluoride) in place of the red, mercuric oxide employed in Example 1. The results of the conversion of the starting materials and selectivity to the desired 2,3-dichloro-5-(trifluoromethyl)pyridine are listed in Table 1.

TABLE 1

| Reagent | Reaction time (hr) | Conversion (%)[a] | Selectivity (%)[a] |
| --- | --- | --- | --- |
| HgO (yellow) | 15 | 100 | 98 |
| HgO (red) | 22 | 99 | 97 |
| HgF₂ | 10 | 98 | 98 |
| AgF | 17 | 99 | 94 |
| Ag₂CO₃ | 30 | 100 | 97 |
| Ag₂O | 30 | 98 | 98 |
| AgF₂ | 34 | 98 | 97 |
| HgCl₂ | 24 | 22 | —* |

[a]denotes conversion and selectivity as indicated by standard gas-liquid chromatography (GLC)
*"—" indicates that at the specific reaction conditions no trifluoromethyl)pyridine compound was formed even though the trichloromethyl group was fluorinated to some extent as indicated by, a 22% conversion.

EXAMPLE 3

The gleaming white precipitate (HgCl₂ by-product) formed in Example 1 was treated with 10% aqueous NaOH to form HgO which was then available for recycle.

EXAMPLE 4

Substantially the same procedure of Example 1 was employed except that 2-chloro-5-(trichloromethyl)pyridine (40 g) was employed as the starting material, 100 g of HF was mixed with the 2-chloro-5-(trichloromethyl)pyridine, 56.3 g of red mercuric oxide was employed as a precursor compound and the reaction was allowed to run for 18 hours. The reaction resulted in the formation of 2-chloro-5-(trifluoromethyl)pyridine. Analysis, via standard gas-liquid chromatography procedures, indicated approximately 100 percent conversion of the starting material, and a yield of 75.4 percent of theoretical. 24.6 Percent of the resulting product was 2-chloro-5-(chlorodifluoromethyl)pyridine based upon analysis of the product.

I claim:

1. A method of preparing a (trifluoromethyl)pyridine compound in a highly selective manner which comprises contacting in the liquid phase a (trichloromethyl)pyridine compound with a stoichiometric amount of HgF₂, Hg₂F₂, AgF or AgF₂ in the presence of from about 4 to about 18 molar equivalents of hydrogen fluoride per molar equivalent of (trichloromethyl)pyridine compound at a temperature of from −20° C. to 50° C.

2. The method of claim 1 wherein said hydrogen fluoride is anhydrous.

3. The method of claim 1 wherein said mercury or silver fluorinating agent is formed in situ.

4. The method of claim 3 wherein said fluorinating agent is formed in situ by slowly adding mercuric oxide, mercuric carbonate, silver carbonate, or silver oxide to a mixture of the (trichloromethyl)pyridine compound and the hydrogen fluoride.

5. The method of claim 4 wherein said reaction is carried out at a temperature below about 50° C. at ambient atmospheric pressure.

6. The method of claim 5 wherein the (trifluoromethyl)pyridine compound prepared is 2,3-dichloro-5-(trifluoromethyl)pyridine and said (trichloromethyl)pyridine compound is 2,3-dichloro-5-(trichloromethyl)pyridine.

7. The method of claim 6 wherein said fluorinating agent is mercuric fluoride formed in situ by the addition of mercuric oxide to 2,3-dichloro-5-(trichloromethyl)pyridine and hydrogen fluoride.

8. The method of claim 6 wherein said fluorinating agent is silver fluoride formed in situ by the addition of silver carbonate to 2,3-dichloro-5-(trichloromethyl)pyridine and hydrogen fluoride.

9. The method of claim 6 wherein said fluorinating agent is silver fluoride formed in situ by the addition of silver oxide or silver carbonate to 2,3-dichloro-5-(trichloromethyl)pyridine and hydrogen fluoride.

10. The method of claim 6 wherein said hydrogen fluoride is present in an amount in the range of from about 4 to about 18 molar equivalents per molar equivalent of 2,3-dichloro-5-(trichloromethyl)pyridine.

11. The method of claim 6 wherein said hydrogen fluoride is present in an amount of about 9 molar equivalents per molar equivalent of 2,3-dichloro-5-(trichloromethyl)pyridine.

12. The method of claim 5 wherein the (trifluoromethyl)pyridine compound prepared is 2-chloro-5-(trifluoromethyl)pyridine and said (trichloromethyl)pyridine compound is 2-chloro-5-(trichloromethyl)pyridine.

13. The method of claim 12 wherein said fluorinating agent is mercuric fluoride formed in situ by the addition of mercuric oxide to 2-chloro-5-(trichloromethyl)pyridine and hydrogen fluoride.

14. The method of claim 12 wherein said fluorinating agent is silver fluoride formed in situ by the addition of silver carbonate to 2-chloro-5-(trichloromethyl)pyridine and hydrogen fluoride.

15. The method of claim 12 wherein said fluorinating agent is silver fluoride formed in situ by the addition of silver oxide or silver carbonate to 2-chloro-5-(trichloromethyl)pyridine and hydrogen fluoride.

16. The method of claim 12 wherein said hydrogen fluoride is present in an amount in the range of from about 4 to about 18 molar equivalents per molar equivalent of 2-chloro-5-(trichloromethyl)pyridine.

17. The method of claim 12 wherein said hydrogen fluoride is present in an amount of about 9 molar equivalents per molar equivalent of 2-chloro-5-(trichloromethyl)pyridine.

18. The method of claim 1 wherein said (trifluoromethyl)pyridine compound is a $\beta$-(trifluoromethyl)pyridine compound prepared from a $\beta$-(trichloromethyl)pyridine compound.

19. The method of claim 18 wherein said $\beta$-(trifluoromethyl)pyridine compound and said $\beta$-(trichloromethyl)pyridine compound optionally contain 1, 2, or 3 chlorine atoms on the pyridine ring.

* * * * *

UNITED STATES PATENT AND TRADEMARK OFFICE
CERTIFICATE OF CORRECTION

PATENT NO. : 4,567,273

DATED : January 28, 1986

INVENTOR(S) : Alexander P. Fung

It is certified that error appears in the above-identified patent and that said Letters Patent is hereby corrected as shown below:

Column 3, line 3, "cyclinders" should read --cylinders--.
Column 6, line 17, "no trifluoromethyl)pyridine" should read --no (trifluoromethyl)pyridine--; line 19 "by, a" should read --by a--.

Signed and Sealed this

Thirtieth Day of September 1986

[SEAL]

Attest:

DONALD J. QUIGG

Attesting Officer

Commissioner of Patents and Trademarks